United States Patent [19]
Pylkki et al.

[11] Patent Number: 5,441,343
[45] Date of Patent: Aug. 15, 1995

[54] THERMAL SENSING SCANNING PROBE MICROSCOPE AND METHOD FOR MEASUREMENT OF THERMAL PARAMETERS OF A SPECIMEN

[75] Inventors: Russell J. Pylkki, Arcadia; Marc Schuman, San Francisco; Paul E. West, Cupertino, all of Calif.

[73] Assignee: Topometrix Corporation, Santa Clara, Calif.

[21] Appl. No.: 127,661

[22] Filed: Sep. 27, 1993

[51] Int. Cl.[6] .......................... G01K 7/00; G01K 3/06; G01N 25/18; G01B 9/04
[52] U.S. Cl. ..................................... 374/137; 374/44; 374/124; 374/142; 374/164; 250/307; 73/105; 356/376
[58] Field of Search ................. 374/44, 124, 137, 120, 374/142, 121, 164; 250/330, 306, 307; 73/105; 356/376

[56] References Cited

U.S. PATENT DOCUMENTS

| | | | |
|---|---|---|---|
| 3,531,642 | 9/1970 | Barnes et al. | 374/124 |
| 4,379,461 | 4/1983 | Nilsson et al. | 374/124 |
| 4,747,698 | 5/1988 | Wickramasinghe et al. | 374/6 |
| 4,854,730 | 8/1989 | Fraden | 374/164 |
| 5,054,936 | 10/1991 | Fraden | 374/164 |
| 5,108,193 | 4/1992 | Furubayashi | 374/164 |
| 5,356,218 | 10/1994 | Hopson et al. | 374/137 |

FOREIGN PATENT DOCUMENTS 1330590  5/1963  France ................................ 374/164

OTHER PUBLICATIONS

A. Majumdar, et al.; "Thermal imaging using the atomic force microscope"; May 17, 1993; pp. 2501-2503 [*Appl. Phys. Lett.*, 62 (20)].

M. Nonnenmacher, et al.; "Scanning probe microscopy of thermal conductivity and subsurface properties"; Jul. 13, 1992; pp. 168-170 [*Appl. Phys. Lett.* 61 (2)].

C. C. Williams, et al.; "Scanning thermal profiler"; Dec. 8, 1986; pp. 1587-1589 [*Appl. Phys. Lett.* 49 (23)].

C. C. Williams, et al.; "High Resolution Thermal Microscopy"; 1986; pp. 393-397 [*Ultrasonics Symposium*].

S. Corrsin; "Turbulence: Experimental Methods."; 1963; pp. 525-589 [*Handbich Der Physik Springer Verlag, Berlin*, 8 (2)].

Joseph A. Stroscio, et al.; "STM and Some Extensions"; 1993; pp. 82-87 [*Scanning Tunneling Microscopy*, vol. 27].

R. W. Powell; "Thermal Conductivity Determinations by Thermal Comparator Methods"; 1969; pp. 274-338 [*Thermal Conductivity*, Tye R. P. ed].

Anthony Auerbach, et al.; "Temperature Measurement and Control of Small Volumes: Applications for Single Channel Recording"; 1986; pp. 190-206 [*Methods in Enzymology*, vol. 124].

(List continued on next page.)

*Primary Examiner*—Diego F. F. Gutierrez
*Attorney, Agent, or Firm*—Fulwider Patton Lee & Utecht

[57] ABSTRACT

The scanning thermal probe microscope measures a thermal parameter such as thermal conductivity or temperature of surface contours of a specimen with a thermal sensor maintained in thermal communication with the surface of the specimen and maintained at a temperature different than that of the specimen. The thermal sensor is disposed on the free end of a cantilever arm in thermal communication with the probe. A thermal feedback bridge circuit can maintain the thermal sensor at a constant temperature by heating or cooling the sensor, and provides a signal for determining the heat transfer between the probe and the specimen. The cantilever arm includes first and second legs of electrically conductive material, and the thermal sensor comprises a narrowed portion of the conducting material having a relatively high temperature coefficient of resistance.

9 Claims, 4 Drawing Sheets

OTHER PUBLICATIONS

C. C. Williams, et al.; "Photothermal Imaging with Sub-100-nm Spatial Resolution"; Jul. 27-30, 1987; pp. 364-369 [*Photoacoustic and Photothermal Phenomena Proceedings of the 5th International Topical Meeting, Heidelberg, Fed. Rep. of Germany*].

Y. Marting, et al.; "Tip-Techniques For Microcharacterization of Materials"; Oct. 5, 1987; pp. 3-8 ]*Scanning Microscopy*, vol. 2, No. 1].

H. K. Wickramasinghe; "Near-Field Thermal Microscopy"; 1991; pp. 214-219 [*Scanning Tunneling Microscopy II: Further Applications and Related Scanning Technology*].

C. C. Williams, et al.; "Scanning chemical potential microsope: A new technique for atomic scale surface investigation"; Aug. 20, 1990; pp. 537-540 [*J. Vac. Science Technology* B 9 (2)].

M. Nonnenmacher, et al.; "Kelvin probe force microscopy"; Apr. 27, 1991; pp. 2921-2923 [*Appl. Phys. Lett* 58 (25)].

K. Dransfeld, et al.; "The heat transfer between a heated tip and a substrate: fast thermal microscopy"; Aug. 4, 1988; pp. 35-42 [*Journal of Microscopy*, vol. 152, Pt 1].

Yogesh B. Gianchandani; "A Bulk Silicon Dissolved Wafer Process for Microelectromechanical Devices"; Jun. 30, 1992; pp. 77-85 [*Journal of Microelectromechanical Systems*, vol. 1, No. 2].

Jianbin Xu, et al.; "On the Energy Dissipation In Field Emission and Tunneling Microscopy"; 1993; pp. 89-100 [*Nanosources and Manipulation of Atoms Under High Field and Temperatures: Applications*].

Jianbin Xu; [*Heat Transfer between Two metallic Surfaces at Small Distances*]Mar. 1993; pp. 1-88.

TSI, St. Paul, Minn. Manufacturer of hot-wire and hot-film probes; [*Hot Film and Hot Wire Anemometry Theory and Application*](No Date).

THERMAL SENSING SCANNING PROBE MICROSCOPE AND METHOD FOR MEASUREMENT OF THERMAL PARAMETERS OF A SPECIMEN

BACKGROUND OF THE INVENTION

1. Field of the Invention

This invention relates generally to scanning probe microscopy, and more particularly concerns a scanning probe microscope with a constant temperature sensor for measuring thermal parameters of a specimen such as surface temperature or thermal conductivity.

2. Description of Related Art

Scanning probe microscopes are useful for imaging objects as small as atoms. Scanning probe microscopy is closely related to scanning tunneling microscopy and the technique of stylus profilometry. However, in a scanning probe microscope, such as an atomic force microscope, a laser beam is typically deflected by a reflective lever arm to which the probe is mounted, indicative of vertical movement of the probe as it follows the contours of a specimen. The deflection of the laser beam is typically monitored by a photodetector in the optical path of the deflected laser beam, and the specimen is mounted on a stage moveable in minute distances in three dimensions. The specimen can be raster scanned while the vertical positioning of the probe relative to the surface of the specimen and the force between the probe and the specimen are maintained substantially constant by a feedback loop with the photodetector controlling the vertical positioning of the specimen.

It has also been found that the topography and surface characteristics of a specimen can be obtained by scanning thermal sensors. One such technique utilizes a noncontacting scanning thermal profiler for investigating surface structures of materials. A scanning probe is heated to a constant temperature and scanned at an approximately constant short distance above a specimen surface. The probe comprises a bimetallic thermocouple for heating the probe and sensing the temperature of the probe. When the heated probe is in close proximity to the surface of the specimen, the temperature of the probe is reduced by thermal coupling between the probe and the specimen, which acts as a heat sink. Current to the thermocouple is constant, so that temperature of the probe is maintained constant by adjusting the vertical position of the probe as it follows the surface contours of the specimen. However, since the probe utilizes a constant current, constant heat source, accurate measurement of changes in temperature involve a delay for allowing the probe to stabilize thermal equilibrium. In addition, since the probe is not permitted to contact the surface of the specimen, the resolution of the system is poor, and the system does not permit measurement of thermal conductivity of the surface structure of the specimen.

One technique for measuring thermal conductivity and subsurface properties of conductors and thin insulating films deposited on conductors utilizes a noncontact scanning Kelvin probe force microscope, which employs capacitance between the probe and the specimen and a temperature dependent voltage difference. The probe is positioned a distance of 2–5 nm from the surface of the specimen, and the probe is heated to approximately 70° above ambient temperature. An electrochemical potential difference between the probe and the surface of the specimen is measured, and heating of the probe or the specimen changes the measured potential difference. However, it would be desirable to provide a system that allows for measuring thermal conductivity of nonconductive materials as well as conductive materials, particularly where both nonconductive and conductive materials are both present in a specimen.

Thermal imaging with an atomic force microscope has also been accomplished using a thermocouple junction as the probe tip. The temperature of the surface of the specimen is obtained by maintaining a reference junction at a constant temperature, and measuring the thermoelectric voltage generated by the thermocouple at the surface of the specimen. Measurement of temperature differences between the probe and the specimen are achieved by heating the specimen. However, it would be desirable to provide a scanning probe microscope with a sensor that is self-temperature regulating, to maintain a constant temperature of the probe, to provide a temperature difference between the probe and the specimen for measuring thermal parameters of the specimen. It has been found that such existing heated probe techniques are generally not capable of measuring thermal conductivity with high resolution over the surface of heterogeneous materials, such as a material composed of diamond, copper, and graphite, and more particularly are not capable of measuring thermal conductivity at the fine boundaries between the materials in such a heterogeneous material. The present invention meets these needs.

SUMMARY OF THE INVENTION

Briefly, and in general terms, the present invention provides for a scanning probe microscope with a thin film or thin wire self-heating or self-cooling resistive sensor, for determining thermal properties of conductive or non-conductive specimens, and for determining topography of a specimen for producing a high resolution image of the specimen surface contours.

The thermal sensing scanning probe microscope of the invention utilizes a standard scanning probe microscope for bringing the probe of the microscope into contact with the surface of the specimen, controlling the contact force of the probe, and scanning the probe across the surface of the specimen. Thermal and topographical data can be obtained and stored simultaneously with the position of the probe on the surface of the specimen, for imaging and analysis.

The sensor consists of a single element that is self-heating or self-cooling, greatly simplifying fabrication of the sensor, can be fabricated on a scanning probe microscope cantilever, and can be used on standard scanning probe microscopes without major modification. The small dimensions and proximity of the sensor to the substrate minimizes the thermal gradient layer in the probe and the amount of heat necessary for operation of the sensor, and minimizes the amount of "thermal drift" due to thermal expansion or contraction. The small dimensions of the sensor also minimize the thermal mass of the sensor, minimizing sensor response time.

In one preferred embodiment, a thermal sensing scanning probe microscope according to the principles of the invention utilizes a thin conductive self-heating or self-cooling resistive sensor in thermal communication with probe of the microscope. The temperature of the sensor is regulated by a bridge circuit that controls current passing through the sensor, to regulate the temperature of the sensor by Joule heating or Peltier cooling. The sensor is maintained at a constant temperature different from that of the specimen, and is in thermal communication with the probe, so that when the probe is brought into contact with the surface of the specimen, heat flows between the probe and the specimen.

As heat is transferred between the sensor and the specimen, the current ratio passing through the parallel legs of the bridge circuit changes, causing a change in the voltage ratio at the midpoint of the bridge legs. Comparison of the voltages at the midpoint of each leg generates an error signal that is used in a feedback circuit to change the power applied to the bridge to maintain the resistance of the sensor constant and to maintain the temperature of the sensor constant. The power necessary to keep the sensor at a constant temperature is a function of the temperature of the surface of the specimen and the thermal conductivity of the specimen, and is determined from a measurement of the voltage of the bridge circuit, and can be used as an indication of thermal conductivity or temperature of the surface of the specimen as a function of the position of the scanning probe relative to the surface of the specimen.

The present invention provides for a scanning thermal probe microscope for measuring a thermal parameter such as thermal conductivity of the surface of a specimen, comprising a probe having a distal tip for contacting the surface contours of the specimen, and thermal sensor means in thermal communication with the probe for measuring the thermal parameter. Thermal feedback means are electrically connected to the thermal sensor means for maintaining the thermal sensor means at a constant temperature different from the given temperature of the specimen, in a preferred embodiment. Heat transfer indicator means are also electrically connected to the feedback means for generating an electrical heat transfer signal providing an indication of heat transfer between the probe and the specimen.

The microscope also includes a cantilever arm support member and a cantilever arm bearing the probe, scanning means for scanning the specimen for examination relative to the probe and for determining position of the probe relative to the surface of the specimen, deflection measuring means mounted relative to the cantilever arm support member for measuring deflection of the cantilever arm, generating a deflection signal indicative of deflection of the cantilever arm, and probe position control feedback means for maintaining the probe in contact with the surface contours of the specimen with a constant force. The microscope also preferably includes storage means for storing the electrical heat transfer signal. The deflection measuring means can further generate output signal data indicative of elevation of the surface contours of the specimen, and the storage means can further store the output signal data indicative of elevation of the surface contours of the specimen, to provide simultaneous measurement of thermal properties and contours of the surface of the specimen.

In one preferred embodiment, the cantilever arm includes first and second legs coated with a conducting material, and the thermal sensor means comprises a narrowed portion of the conducting material having a relatively high temperature coefficient of resistance. The cantilever arm support member preferably comprises a first portion of electrically conductive material electrically connected to the first leg of the cantilever arm, and a second portion of electrically conductive material electrically isolated from the first portion of electrical conductive material electrically connected to the second leg of the cantilever arm.

The thermal feedback means comprises an electrical bridge circuit, and the heat transfer indicator means comprises means for measuring voltage across the bridge circuit, and means responsive to the voltage across the bridge for determining power drawn by the thermal sensor to maintain the thermal sensor temperature constant.

In another preferred embodiment, the cantilever arm is formed from an electrically conductive wire, and the thermal sensor comprises a narrowed portion of the wire having a relatively high temperature coefficient of resistance. Where the probe is formed from electrically conductive wire, the narrowed portion of the wire having a relatively high temperature coefficient forms the distal tip.

In a third preferred embodiment, where the sensor can be cooled to remain at a constant temperature lower than the temperature of the specimen, the cantilever arm support member is coated with a first electrically conductive material divided into first and second sections electrically isolated from each other, and the cantilever arm comprises a first leg comprised of a first electrically conductive material connected to the first section of the first electrically conductive material, and a second leg formed of a second electrically conductive material. The thermal sensor means comprises a narrow cooling junction of the first and second electrical conductors of the first and second legs having a relatively high temperature coefficient of resistance, and the second electrically conductive material of the second leg is electrically connected to the second section of the first electrically conductive material of the cantilever arm support member at a heating junction spaced apart from the narrow junction forming the thermal sensor means.

These and other aspects and advantages of the invention will become apparent from the following detailed description, and the accompanying drawing, which illustrates by way of example the features of the invention.

DETAILED DESCRIPTION OF A PREFERRED EMBODIMENT

Constant current, constant heat thermocouple scanning probe devices used to scan thermal characteristics of the surface of a specimen suffer from a time lag necessitated by stabilization of the thermal equilibrium of the probe. In addition, such noncontact scanning devices do not readily allow measurement of thermal conductivity of the surface structure of specimens that are not electrically conductive. Using a thermocouple junction as the probe tip of an atomic force microscope allows measurement of temperature differences between the probe and the specimen, but such devices are not self-temperature regulating to maintain a constant temperature of the probe, to provide a temperature difference between the probe and the specimen for measuring thermal parameters of the specimen.

As is illustrated in the drawings, the invention is embodied in a scanning probe microscope 10 for measuring thermal properties of the surface of a conductive and non-conductive specimen 12, using thin film or thin wire self-heating or self-cooling resistive sensor techniques, and for determining topography of the specimen for producing a high resolution image of the specimen surface contours. The microscope is particularly useful in determining thermal conductivity over the surface of heterogeneous materials, such as a material composed of diamond, copper, and graphite, and for determining thermal conductivity at the fine boundaries between the materials in a heterogeneous material. The microscope would be useful, for example, in testing the thermal conductivity of materials such as ceramics, high temperature resistant materials, and composites.

Figure 1:
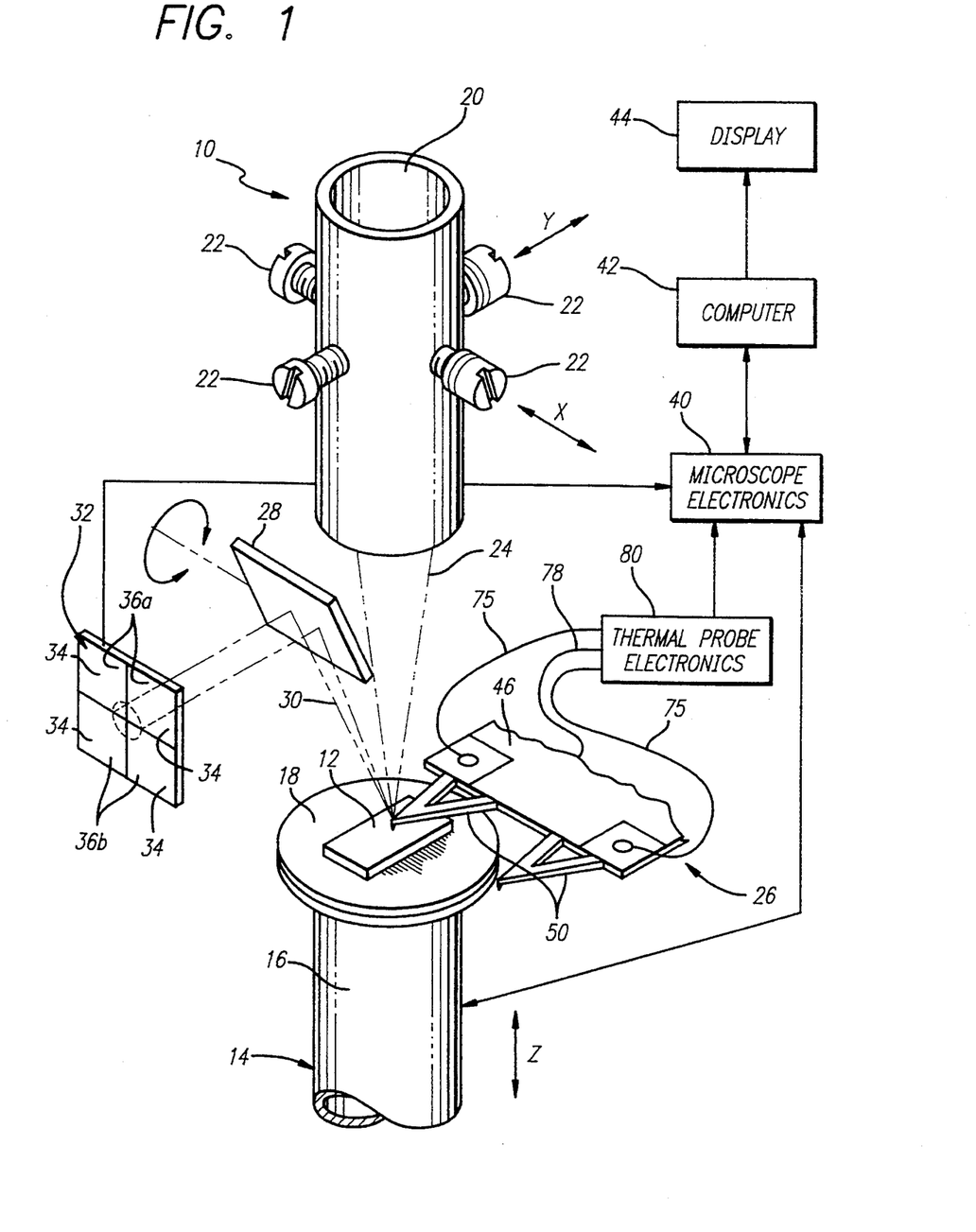
FIG. 1 is a simplified diagram of the scanning probe microscope for measuring thermal parameters of a specimen according to the principles of the invention.

The microscope, illustrated in simplified form in FIG. 1, includes a scanner 14 for mounting of the specimen for examination, raster scanning the specimen in X and Y directions relative to the body, as shown by the arrows, that is, horizontally in two dimensions or degrees of freedom, and for moving the specimen in a vertical or Z dimension or degree of freedom relative to the body, as shown by the arrow. The scanner typically includes a piezo tube 16 with a support stage 18 for the specimen, and is typically driven in the X, Y and Z dimensions by piezoelectric transducer elements (not shown).

A laser light source 20 such as a laser diode with associated optics, is mounted in the upper portion of the body (not shown) of the microscope and can be aligned and aimed by adjustment screws 22 for producing a focused laser beam 24. One preferred laser diode is a 3 milliwatt laser diode which produces a beam in the 670 nm range, and is commercially available. The laser beam 24 is directed at and deflected by the reflective optical lever arm 26. A planar mirror 28 is typically mounted in the interior of the body of the microscope to reflect the deflected beam 30 from the optical lever arm to a photodetector 32 mounted to the microscope for receiving the deflected laser beam.

The photodetector 32 preferably generates an electrical output signal in response to the deflected laser beam indicative of the degree of deflection of the laser beam by the optical lever arm. The photodetector is typically formed as an array of four photosensors 34, in which the top pair 36a is coupled to provide a combined signal, and the bottom pair 36b is coupled to provide a combined signal. The deflected laser beam is typically targeted at a central point between the top and bottom portions of the photodetector, and the combined signals from these portions are processed to generate output signals which can be compared to produce a differential error signal by the microscope feedback electronics 40, such as are commercially available from Topometrix Corporation. Additionally, the left and right halves of the array of photosensors may be summed for scanning in a frictional force mode.

The microscope electronics are electrically connected to the photodetector to receive the output signals indicative of deflection of the laser beam from the optical lever arm, and to generate an error signal indicative of a variance from the constant amount of force of the probe tip against the specimen surface. The microscope electronics are electrically connected to the scanner, which is responsive to the error signal for raising and lowering the specimen with respect to the probe tip, for increasing or decreasing the force of the probe tip against the specimen surface to maintain constant contact and a substantially constant amount of force of the probe tip against the specimen surface. The microscope electronics also provide probe position data to the computer 42, which includes a processor and memory for analyzing and storing topographical information from the scanning of the surface of the specimen, that can in turn be viewed on a display 44. Although the thermal sensing scanning probe microscope has been described as operating in a constant force mode, it is also possible to operate the microscope in a variable force mode, as is well known to those skilled in the art. In addition, although the microscope is currently preferably operated to maintain constant contact of the probe with the surface of the specimen, the microscope electronics can also maintain the probe in thermal communication with the surface of the specimen without contacting the specimen. For example, it may be desirable to measure thermal conductivity or temperature of the surface of the specimen in a contact mode, and to draw the tip of the probe away from the surface, or to skim the tip over the surface of the specimen, at a distance of 0.5 microns, for example, for additional measurements. However, it is preferable to maintain thermal communication of the probe with the specimen by maintaining a distance between the tip of the probe and the surface of the specimen of no more than about one micron.

With reference to FIGS. 1 to 4, in one preferred embodiment, the optical lever arm 26 comprises a cantilever arm support member 46, typically adhesively bonded by epoxy, or a similar appropriate adhesive, to a magnetic steel member 48, which is magnetically mounted to the body of the microscope. The optical lever arm currently typically includes dual cantilever arms 50 having different force constants, for convenience in choosing using the microscope to examine a variety of different material with different hardness. Each cantilever arm preferably has a reflective top surface, and is typically formed in the shape of a triangle from a first outer leg 52 and a second inner leg 54 extending from one end of the cantilever arm support member. The legs of the cantilever arm are typically about 18 microns wide, about one micron thick, and about 200 microns long, and are about 120 microns apart at the proximal end 56 of the cantilever arm adjacent to the cantilever arm support member.

Figure 4:
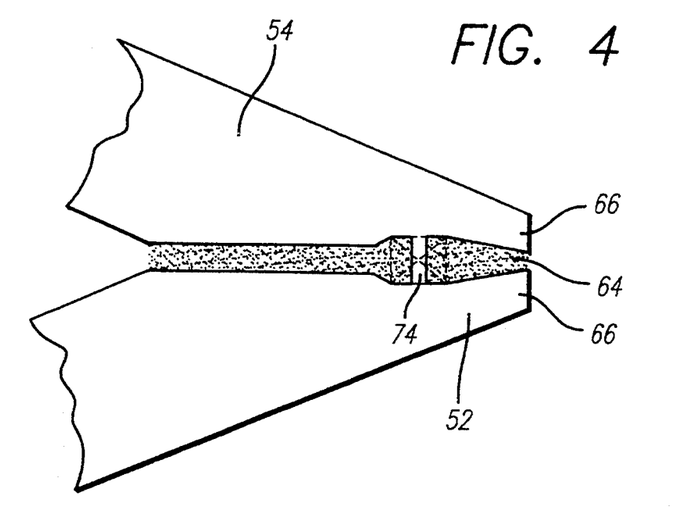
FIG. 4 is an enlarged view of the inset position of FIG. 3, showing the single element thermal sensor in greater detail.

At the distal free end 58 of the cantilever arm where the legs of the triangular cantilever arm come together, is a probe 60 having a distal pyramidal shaped tip 62 extending approximately perpendicular to the legs of the cantilever arm, adapted to contact and follow the surface contours of the specimen. The cantilever arm support member and the cantilever arms are typically formed from a common material.

Figure 6:
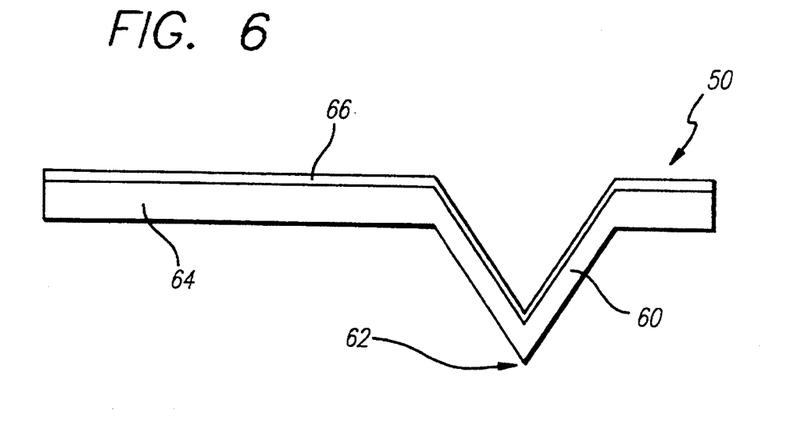
FIG. 6 is a cross-sectional view of a portion of the tip of the cantilever of FIG. 4.

In one preferred form of the support member and cantilever arms, a wafer of silicon is coated with a layer of silicon nitride approximately one micron thick, patterned, and etched to form the cantilever arms of one piece with the support member. Strengthened glass such as borosilicate glass commonly sold under the trademark "PYREX" from Corning can also be bonded to the silicon nitride by application of high voltage. The cantilever arm typically bows and flexes as much as 30° as the probe tip is pressed against the surface of the specimen, deflecting the laser beam. The cantilever arm support member and the reflective cantilever arm can be etched from other materials as well, such as silicon, which can be etched or lend themselves to fine machining and which can provide a reflective surface, such as are well known to those skilled in the art of manufacturing of integrated circuit chips. When the cantilever arm support member and cantilever arm are constructed of silicon nitride, the probe typically is formed in a pyramidal shape from a pit cut in the layer of silicon nitride, and is typically hollow, as is illustrated in FIG. 6. The cantilever arm support member and cantilever can also be constructed of other rigid, resilient materials, such as silicon, suitable plastics, or the like.

As can best be seen in FIG. 6, the silicon nitride layer 64 of the cantilever arms is also coated with a layer of conductive material 66, such as platinum, although other conductive metals such as platinum-iridium alloy or tungsten may also be suitable. Conductive materials having a high temperature coefficient of resistance are preferred, as will be explained further below. Platinum, having a temperature coefficient of resistance of about 0.0039/°C. is currently most preferred, having good oxidation resistance as well. Tungsten has a temperature coefficient of resistance of about 0.0036 to about 0.0048/°C., and is strong, but has poorer oxidation resistance. Nickel, having a temperature coefficient of resistance of about 0.0064/°C., is also useful, and an alloy of platinum and 10% rhubidum, having a temperature coefficient of resistance of about 0.0016/°C. to about 0.0017/°C., is also suitable. Platinum-iridium alloy has good oxidation resistance, but has a lower temperature coefficient of about 0.0007 to about 0.00085/°C.

Figures 2, 3:
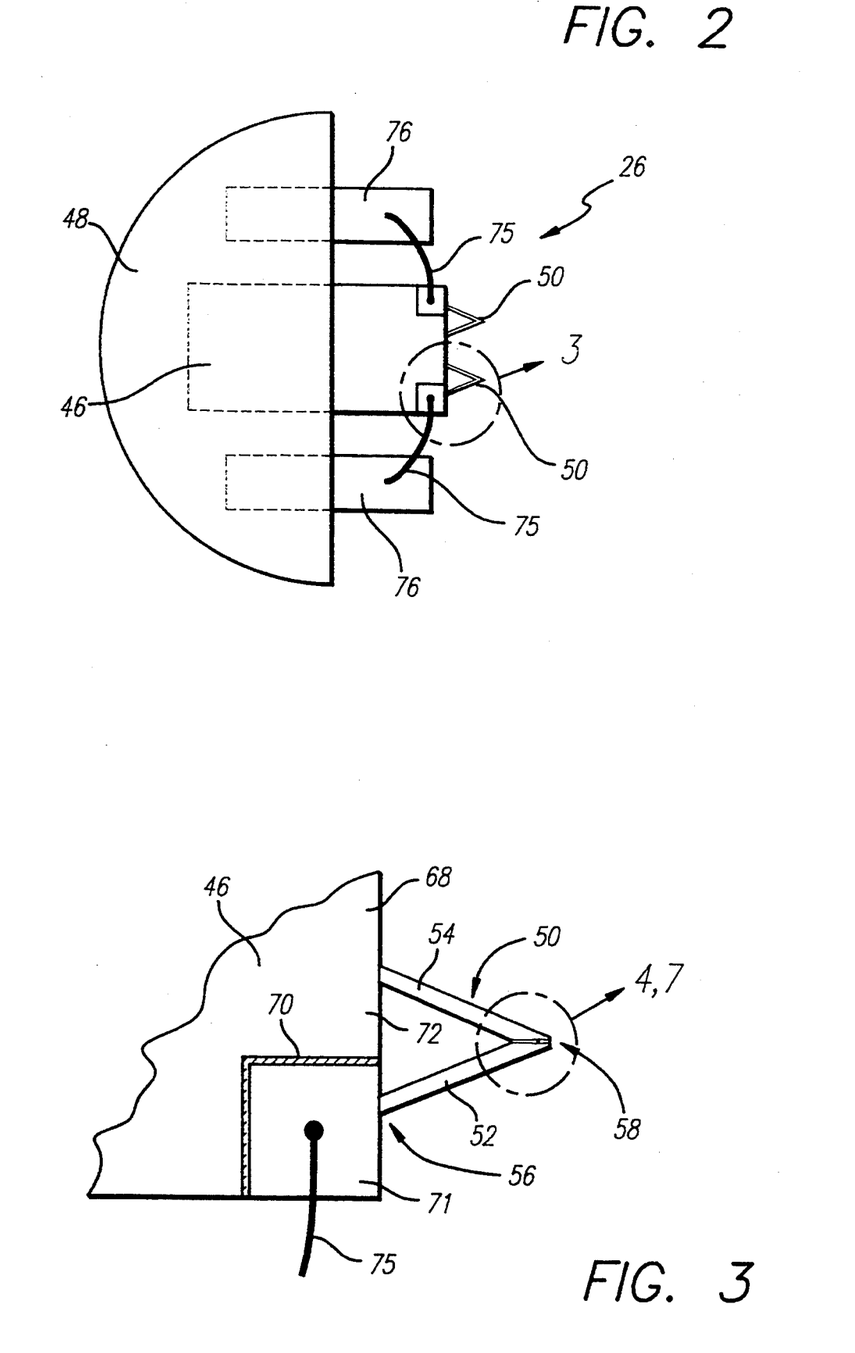
FIG. 2 is top plan view of a cantilever support structure of a scanning probe microscope showing one embodiment of a scanning probe and thin film self-heating resistive sensor according to the principles of the invention.
FIG. 3 is an enlarged view of the inset portion of FIG. 2, showing the electrical isolation of the arms of the cantilever and single element thermal sensor in greater detail.

The cantilever arm support member 46 also preferably includes a coating of a conductive material 68, such as gold or platinum, over the silicon nitride layer shown exposed in FIG. 3, although other conductive metals may also be appropriate. The coating of conductive materials is typically deposited on the silicon nitride layer of the cantilever arm support member and the cantilever arms by evaporative deposition or sputter deposition.

A narrow channel in the top coating of conductive material on the silicon nitride layer of the cantilever arm support member and the cantilever arms is preferably formed at 70, to electrically isolate a portion 71 of the conductive layer on the cantilever arm support member contiguous with and electrically connected with the conductive material on the outer first leg 52 of the cantilever arm from the middle portion 72 of the conductive material on the cantilever arm support member that is contiguous with and electrically connected to the conductive material on the inner second leg 54 of the cantilever arm. The channel is preferably formed by masking a strip over the cantilever arm support member before the conductive material is deposited on it, but the channel may also be formed by a focused ion beam once the conductive material has been deposited. The placement of the channel 70 through the conductive material on the cantilever arm support member as illustrated thus forms an electrical path through the legs of the cantilever arms.

As is shown in FIG. 4, the conductive material at the union of the two legs of the cantilever arms is also typically cut away by a focused ion beam to form a narrow junction between the two legs of the cantilever arms that is typically approximately 5 microns long, one micron wide, and 100 nm thick, and forms the resistive thermal sensor 74 of the microscope. Electrical leads 75 are connected between the electrically isolated conductive material and conductors 76 electrically connected to the thermal probe electronics 80. As is illustrated in FIG. 1, the conductive material of the cantilever arm support member connected to the inner second legs of the cantilever arms is electrically connected by conductor 78 to the thermal probe electronics 80.

Figure 5:
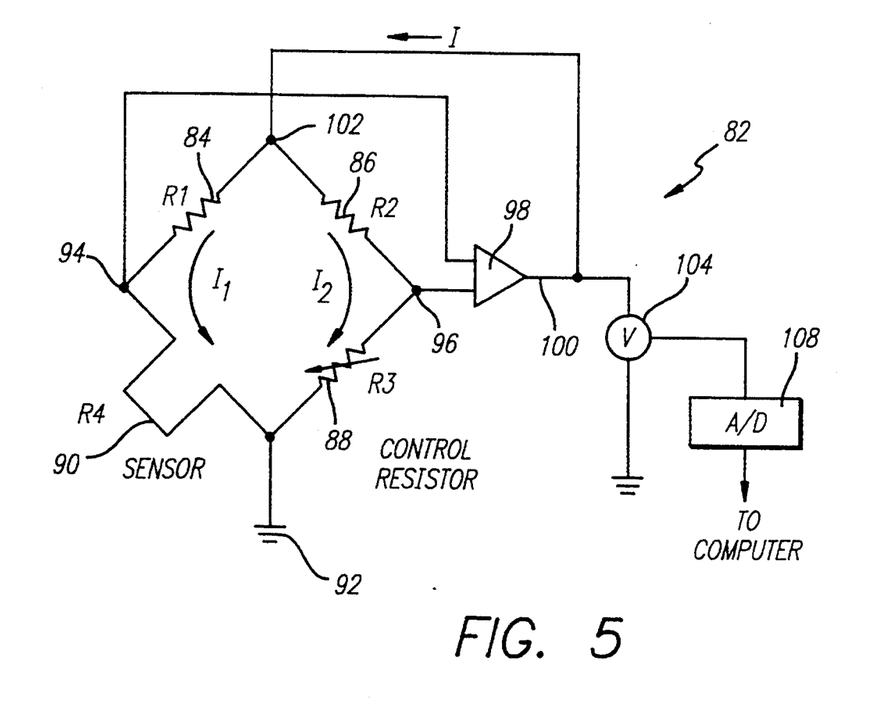
FIG. 5 is a schematic diagram of an electrical bridge circuit for the constant temperature sensor of the invention.

With reference to FIGS. 1 and 5, the thermal probe electronics 80 preferably includes a bridge circuit 82 providing a constant temperature feedback loop for maintaining the sensor at a substantially constant temperature different than that of the specimen. Resistors $R_1$ 84 and $R_2$ 86 have fixed resistances in the circuit, while the resistance of control resistor $R_3$ 88 is adjustable. The sensor 74 provides the fourth sensor $R_4$ 90 in the bridge circuit. The junction between $R_3$ and $R_4$ is connected to ground 92, while junction 94 between $R_1$ and $R_4$ and the junction 96 between $R_2$ and $R_3$ are connected to inputs to the differential amplifier 98, providing an electrical output 100, connected to feed back current to the junction 102 between resistors $R_1$ and $R_2$. One such bridge circuit that is currently preferred is included in the Model 1750 Constant Temperature Anemometer available from TSI of St. Paul, Minn.

As the probe is scanned over a thermally conductive region of the surface, heat will be transferred between the probe and the surface of the specimen. In the embodiment of the sensor illustrated in FIG. 4, the specimen will be at ambient temperature, and the sensor will be maintained at a temperature typically from 10° C. to 80° C. above ambient temperature. The sensor typically has an operating temperature as high as 250° C. The temperature at which the sensor operates in the absence of contact with the surface of the specimen is controlled by the appropriate selection of resistors in the bridge circuit. As heat is transferred from the probe to the surface of the specimen, the sensor will tend to cool, reducing the resistance of the sensor $R_4$ 90 in the bridge circuit, causing the voltage drop across the sensor $R_4$ 90 to decrease, changing the input voltage to the differential amplifier 98. The differential amplifier operates to increase output of the amplifier when the voltage decreases, increasing the current to the sensor to maintain the temperature of the sensor constant. Conversely the differential amplifier operates to decrease output to the bridge circuit when the voltage increases, decreasing the current to the sensor to maintain the temperature of the sensor constant.

The voltage output 104 of the differential amplifier in driving the temperature counterbalancing current through the sensor is typically converted to a digital signal by an analog to digital converter 108, typically placed in the microscope electronics 40, in which form the voltage signal can be stored by the computer 42 as raw data, for analysis. For example, the voltage can be squared by the computer to provide a measure proportional to the amount of power drawn by the sensor. Alternatively, dedicated circuitry could be provided for squaring the voltage signal to provide an output indication of the power drawn by the sensor. With the feedback control of the bridge circuit the resistances are substantially constant, and the voltage across the bridge is directly proportional to the current through the sensor $R_4$. Since power is equal to the square of the voltage divided by the resistance, the square of the current is directly proportional to the power and the instantaneous heat transfer from the sensor. The computer thus can generate and store an output signal indicative of the power drawn as an indication of heat transfer, along with position data from the microscope electronics. Since the heat transfer is a function of not only the thermal conductivity of the specimen but also the temperature of the specimen, it is possible to use the heat transfer data generated from the constant temperature thermal sensor and bridge circuit of the microscope, operated in a constant temperature mode, to measure not only thermal conductivity of the surface structure of the specimen, including a portion of the specimen underlying the surface contours of the specimen, but also temperature variations over the surface of a specimen, particularly of a specimen for which the thermal conductivity is known.

Figure 7:
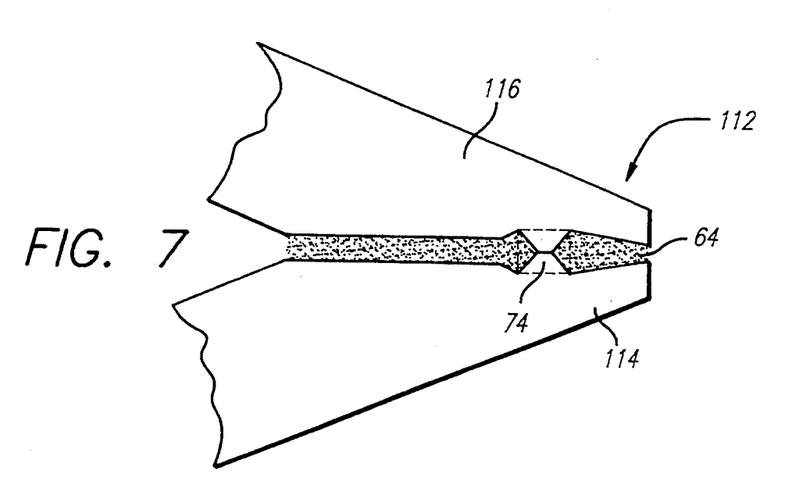
FIG. 7 is an illustration of a preferred embodiment of a self-cooling thermal sensor similar to that of FIG. 4 capable of Peltier cooling for use with a thermal sensing scanning probe microscope according to the principles of the invention.

In another preferred embodiment of the thermal sensing scanning probe microscope, the conductive material on the cantilever arm can be constructed as a Peltier cooling device 112 to be self-cooling, in order to maintain a temperature differential between the sensor and the specimen, such as for measuring thermal conductivity over the surface of a high temperature specimen. With reference to FIG. 7, in this embodiment the outer leg 114 of the cantilever arm is coated with a first metal, and the inner leg 116 of the cantilever arm is coated with a second metal, forming a Peltier junction in the resistive thermal sensor 74 where the two metals interface, for cooling the sensor near the probe. The electrically isolated portions of the cantilever arm support member are also coated with one of the two different metals, which can be platinum and platinum-iridium alloy, for example. Other combinations of metals, such as are suitable for use in thermocouples and that are appropriate for use in the bridge thermal sensing circuit may also be suitable. Depending upon the polarity of the circuit path through one section of the cantilever arm support member to one arm of the cantilever, through the other arm of the cantilever arm back to the other section of the cantilever arm support member, normal direction of flow of current is established, such that the junction of the metal on one .leg of the cantilever arm with a dissimilar metal of the cantilever arm will serve as a Joule heating junction, while the other junction of the dissimilar metals interfacing at the sensor serves as the Peltier cooling junction. By passing current in the direction opposite to this normal direction of flow, the sensor can be operated as a Peltier cooling device, and the sensor can be cooled to maintain the temperature of the sensor at a substantially constant temperature below the temperature of the specimen. The placement of the heating junction should be spaced a sufficient distance from the cooling junction so that the heat produced by the heating junction will not affect the cooling of the sensor. In all other respects, the embodiment of FIG. 7 is substantially the same as in the previously discussed embodiment of the invention.

Figure 8:
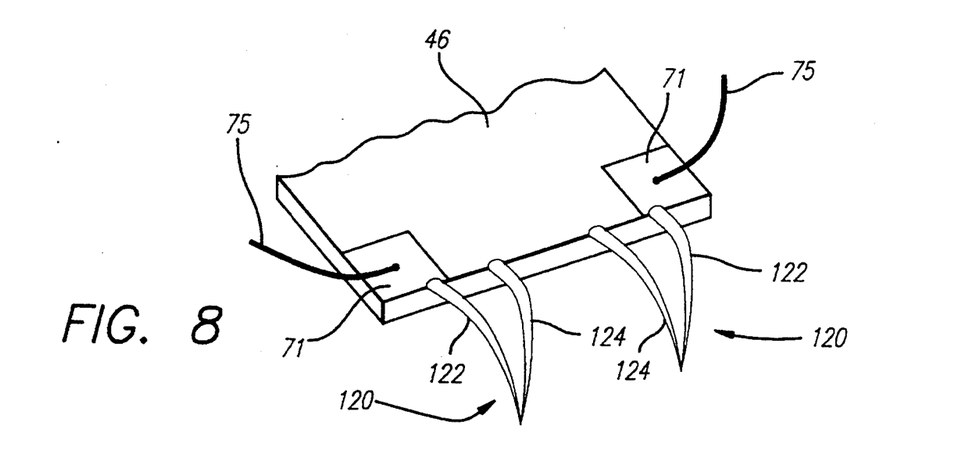
FIG. 8 is an illustration of a preferred embodiment of a thin wire thermal sensor for use with a thermal sensing scanning probe microscope according to the principles of the invention.

In another preferred embodiment of the thermal sensing scanning probe microscope of the invention, the cantilever arm structure 120 can be formed of a thin wire, as is illustrated in FIG. 8. In this embodiment, the cantilever arm, sensor, probe and probe tip are formed as a unitary structure from a thin wire, such as a platinum wire approximately 50 to 75 microns in diameter. Because the platinum wire becomes more flexible as it is thinned, the Wollaston process is used, in which the platinum wire is encased and supported in an outer metallic tube, such as of silver, which is then preferably heated and drawn down to thin the platinum wire inside, so that the platinum wire core is thinned to a diameter of from 12 to 0.5 microns. The silver encased thinned wire can then be shaped as a probe and mounted to the conductive material on the cantilever support structure, such as by welding or soldering, with the outer leg 122 of the cantilever connected to the electrically isolated portion of the cantilever arm support member, and the inner leg 124 connected to the main conductive inner portion of the cantilever arm support member. The silver casing is then etched away, leaving a thinned platinum wire having a resistance suitable for use as a sensor in the thermal sensing, constant temperature bridge circuit. It is also possible to form the thin wire cantilever arm probe and sensor from wires of two different metals, such as platinum and platinum-iridium alloy, and to operate the bimetallic wire probe and sensor as a Peltier cooling device, as described above. In all other respects, the thermal sensing scanning probe microscope of this embodiment is substantially the same as previously described for the other embodiments.

In view of the foregoing, it has been demonstrated that the thermal sensing scanning probe microscope of the invention provides a constant temperature sensor used to scan thermal characteristics of the surface of a specimen that does not suffer from a time lag necessitated by stabilization of the thermal equilibrium of the probe. The use of active thermal feedback to maintain the sensor at a substantially constant temperature greatly enhances the response time of the probe. The constant temperature sensor also allows for determination of a wider range of thermal conductivities at a given operating temperature than is possible with a constant heat or constant current sensor, and prevents sensor burnout in the event of loss of contact of the probe tip with the specimen substrate, especially during operation of the sensor at high temperatures.

In addition, the sensor does not depend on the formation of an electrical junction between the probe and the specimen surface, for either its response or calibration, so that the thermal sensing scanning probe microscope of the invention readily permits measurement of thermal conductivity of the surface structure of specimens that are not electrically conductive. The temperature difference between the tip of the probe and the surface of the specimen can be created by Joule heating or Peltier cooling of the sensor, so that the system of the invention can be utilized in a wide temperature range. The microscope can be used to simultaneously determine the topography and thermal properties of a wide range of conductive and non-conductive materials. Integration of the thermal probe with a scanning probe microscope cantilever allows for control of the contact force of the probe with the specimen surface, allowing for reproducible measurements of thermal properties.

With the constant temperature, thermal sensing scanning probe microscope of the invention, thermal conductivities of approximately 2000 watts/meter-Kelvin (for diamond) to 0.02 watts/meter-Kelvin (for air) are possible. The constant temperature thermal sensing scanning probe microscope is also capable of a high frequency response of 100 kilohertz or more due to the lack of lag time for stabilization of a thermal equilibrium. However, it should be readily apparent that the thermal sensor of the invention can also be modified to measure temperature, by providing a constant current source for the resistive sensor of the microscope. The thermal sensor can be operated in a constant current mode if the current is low enough so that substantially no self-heating of the probe is allowed to occur, as the bridge circuit can be used to determine the temperature of the sensor by the change in resistivity of the sensor as its temperature changes.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. A method for measuring a thermal parameter of a specimen with a scanning thermal probe microscope having a probe having a distal tip for maintaining thermal communication with surface contours along a surface of the specimen, and a thermal sensor in thermal communication with said probe for measuring said thermal parameter, comprising the steps of:

maintaining said thermal sensor at a substantially constant temperature while maintaining a temperature differential between said thermal sensor and said specimen;

maintaining the probe in thermal communication with said surface of said specimen;

generating an electrical heat transfer signal proportional to power required to maintain said thermal sensor at said substantially constant temperature, providing an indication of heat transfer between said probe and said specimen;

scanning said specimen relative to said probe and determining the position of said probe relative to said surface of said specimen; and storing said electrical heat transfer signal and said position of said probe relative to said surface of said specimen.

2. The method of claim 1 wherein said step of maintaining the probe in thermal communication with said surface of said specimen comprises generating output signal data indicative of elevation of the surface contours of said specimen, and further comprising the step of storing said output signal data indicative of elevation of said surface contours of said specimen with said electrical heat transfer signal and said position of said probe relative to said surface of said specimen.

3. The method of claim 1, wherein said step of maintaining said thermal sensor at a substantially constant temperature while maintaining a temperature differential between said thermal sensor and said specimen comprises cooling said thermal sensor.

4. The method of claim 1, wherein said thermal sensor is maintained at a constant temperature by a bridge circuit in which said thermal sensor is electrically connected as a variable resistance resistor in said bridge circuit, and said step of generating an electrical heat transfer signal providing an indication of heat transfer between said probe and said specimen comprises generating a voltage output signal representing voltage across said bridge circuit.

5. The method of claim 4, further comprising the step of squaring said voltage output signal for providing an indication of power drawn by said thermal sensor to maintain said thermal sensor temperature constant.

6. The method of claim 1, wherein said microscope further comprises a cantilever arm support member, a cantilever arm having a proximal end secured to the cantilever support member and a distal free end bearing said probe, and said step of maintaining the probe in thermal communication with said surface of said specimen comprises measuring deflection of said cantilever arm, generating a deflection signal indicative of deflection of said cantilever arm, and generating output signal data indicative of elevation of said surface contours of said specimen.

7. The method of claim 1, wherein said step of measuring a thermal parameter with said thermal sensor comprises measuring thermal conductivity of the surface contours of said specimen.

8. The method of claim 1, wherein said step of measuring a thermal parameter with said thermal sensor comprises measuring temperature of the surface contours of said specimen.

9. The method of claim 1, wherein said step of measuring a thermal parameter with said thermal sensor comprises measuring thermal conductivity of a portion of said specimen underlying the surface contours of said specimen.

* * * * *